United States Patent [19]

Spiess et al.

[11] Patent Number: 5,308,519

[45] Date of Patent: May 3, 1994

[54] TUNGSTEN HEXALDIALKYLDITHIOCARBAMATES, PROCESS FOR THEIR PREPARATION AND OIL COMPOSITIONS CONTAINING THEM

[76] Inventors: Wolfram Spiess, Heinrich-Becker-Strasse 16; Friedrich Franke, Bitzenstrasse 22 A, both of, D-6718 Grünstadt; Rolf Himmelreich, deceased, late of D-6718 Grüstadt; by Margot M. C. Himmelreich, executor, Uhlandstrasse 9; by Petra Himmelreich, heir, Schlesingerstrasse 9, D-6718 all of Grünstadt; by Ralf Himmelreich, heir, Augustastrasse 15, 6900 Heidelberg-Rohrbach, all of Fed. Rep. of Germany

[21] Appl. No.: 950,676

[22] Filed: Sep. 25, 1992

[30] Foreign Application Priority Data

Sep. 25, 1991 [DE] Fed. Rep. of Germany ....... 4131921

[51] Int. Cl.$^5$ .......................................... C10M 135/18
[52] U.S. Cl. .................... 252/46.4; 252/47.5; 556/38
[58] Field of Search ................. 252/46.4, 47.5; 556/38

[56] References Cited

U.S. PATENT DOCUMENTS

| 3,234,129 | 2/1966 | Perilstein | 252/46.4 |
| 3,244,627 | 4/1966 | Smith et al. | 252/33.6 |
| 3,674,824 | 7/1972 | Amidon et al. | 556/38 |
| 3,678,135 | 7/1972 | Mastromatteo et al. | 556/38 |
| 3,707,498 | 12/1972 | Milsom | 556/38 |
| 4,786,423 | 11/1988 | Schroeder | 252/46.4 |
| 4,846,983 | 7/1989 | Ward, Jr. | 252/46.4 |
| 4,849,123 | 7/1989 | Tipton et al. | 252/75 |

FOREIGN PATENT DOCUMENTS

2143768 of 1972 Fed. Rep. of Germany.
8705045 8/1987 PCT Int'l Appl..
8707291 12/1987 PCT Int'l Appl..
404114 5/1977 U.S.S.R..

OTHER PUBLICATIONS

Chemical Abstracts, vol. 108, No. 48081c (1988).
Chemical Abstracts, vol. 73, No. 20969 (1970).

*Primary Examiner*—Ellen M. McAvoy

[57] ABSTRACT

Novel tungsten hexa(dialkyldithiocarbamates) of the general formula I

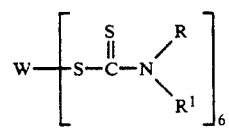

in which R and $R^1$ can be identical or different, branched or straight-chain, saturated or unsaturated alkyl radicals having 1–18 carbon atoms are prepared by a process in which 6 mols of an alkali metal dialkyldithiocarbamate of the general formula II

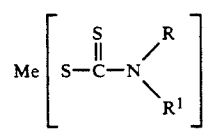

in which R and $R^1$ are as signified above and Me can be sodium, potassium or ammonium, are reacted with 1 mol of tungsten hexachloride in a solvent which is inert with respect to the reaction. The alkali metal chloride or ammonium chloride formed is separated off and the tungsten hexa(dialkyldithiocarbamate) is isolated. The tungsten hexa(dialkyldithiocarbamates) of the invention can be used as additives for prolonging the life of hydraulic oils or permanent gear lubrication oils.

12 Claims, No Drawings

TUNGSTEN HEXALDIALKYLDITHIOCARBAMATES, PROCESS FOR THEIR PREPARATION AND OIL COMPOSITIONS CONTAINING THEM

BACKGROUND OF THE INVENTION

1. Field of the Invention:

This invention relates to tungsten hexa(dialkyldithiocarbamates) as well as to processes for the production of such compounds. The invention also relates to improved lubricating oil and hydraulic fluid compositions containing these compounds.

2. Brief Description of the Prior Art:

In accordance with conventional industrial processes, heavy metal dithiocarbamates are prepared either by double displacement reaction of alkali metal or ammonium dithiocarbamates with heavy metal halides or by reaction of metal oxides with amines and carbon disulfide.

When metal oxides of metals having a valence of 2-4 are used in the the conventional industrial techniques, the reaction yields oxide-free dialkyldithiocarbamates of the formula

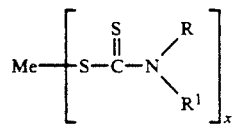

in which x represents the valency of the metal employed, in this case 2-4.

When the reactions are conducted using oxides of metals of higher valency the result is formation of oxide-containing dialkyldithiocarbamate mixtures of the general formula

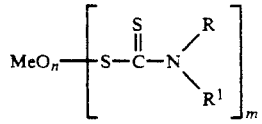

wherein n, m=1-2.

Oxide-free tungsten dithiocarbamates are hitherto unknown.

Accordingly, a need has continued to exist to prepare oxide-free tungsten dithiocarbamates and for a method of preparing them.

SUMMARY OF THE INVENTION

The novel compounds of the invention are tungsten hexa(dialkyldithiocarbamates) of formula I

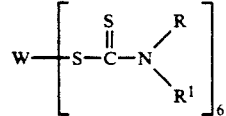

wherein R and $R^1$ can be identical or different, branched or straight-chain, saturated or unsaturated alkyl radicals having 1-18 carbon atoms.

It has now been found that certain compounds of the general formula I can be prepared by reaction of alkali metal dialkyldithiocarbamates with tungsten hexachloride. Since these compounds possess outstanding properties as oil additives, the preparation and provision of the compounds according to the invention represents a substantial improvement over the prior art, especially since a more environmentally benign use of hydraulic oils or gear oils is possible as a result of the improvement in the oil quality. The oil additive compounds of the invention have been found to prolong the life of permanent gear lubricating oils and hydraulic fluids to which they are added.

Accordingly, it is an object of the invention to provide tungsten hexa(dialkyldithiocarbamates).

A further object is to provide a method for preparing tungsten hexa(dialkyldithiocarbamates).

A further object is to provide tungsten hexa(dialkyldithiocarbamates) which are useful as additives for lubricating oils and hydraulic fluids.

A further object is to provide lubricating oils and hydraulic fluids having a longer life.

Further objects of the invention will become apparent from the description of the invention which follows.

DETAILED DESCRIPTION OF THE INVENTION AND PREFERRED EMBODIMENTS

The tungsten hexa(dialkyldithiocarbamates) of the invention are prepared by the following reaction scheme:

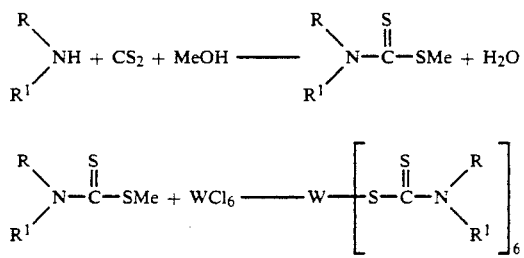

wherein: R and $R^1$ have the signification set forth above, and Me signifies Na, K, or $NH_4$.

The fundamentals of preparing alkali metal dialkyldithiocarbamates are known. In general, the procedure for this preparation is as follows:

Solid sodium hydroxide is dissolved in anhydrous methanol and the dialkylamine is added to this solution. The formation of the sodium dialkyldithiocarbamate is effected by adding carbon disulfide. All reagents are used in stoichiometric amounts, carbon disulfide preferably being maintained in a 10% excess. The mixture is stirred for 1-3 hours at temperatures of 10°-50° C., preferably at about 25° C.

The sodium dialkyldithiocarbamate solution prepared by this procedure can be used directly in further reactions and serves as the starting material for reaction with tungsten hexachloride.

Stoichiometric amounts of tungsten hexachloride are dissolved in anhydrous methanol and reacted with the sodium dialkyldithiocarbamate. The reaction takes place at temperatures of 10°-90° C., preferably at 20°-30° C. and more preferably at about 30° C.

The reaction is weakly exothermic in both steps; therefore no additional heat has to be supplied.

After a reaction time of 2 hours, the alkali metal chloride which has precipitated out is filtered off and the methanol is distilled off under vacuum at a temperature of 50° C. If appropriate, sodium chloride residues are again separated off by filtration from the brown oil obtained in this way.

Instead of methanol, it is also possible to use other anhydrous solvents such as ethanol, butanol, isopropanol, dioxane, tetrahydrofuran or ethylene glycol monoalkyl ether.

The following examples relating to the preparation of the compounds according to the invention are intended to illustrate the invention but not to limit its scope.

EXAMPLE 1

Tungsten hexa(diamyldithiocarbamate)

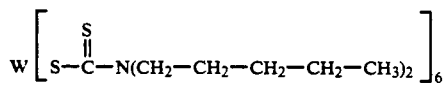

Empirical formula: $C_{66}H_{132}N_6S_{12}W$
Molecular weight: 1578.379

0.576 kg of granulated caustic soda is added to 8 liters of anhydrous methanol and the mixture is stirred until all solid material has dissolved. 2.26 kg of diamylamine are added to the solution and 0.88 liter of carbon disulfide is introduced over a period of 2 hours. The mixture is stirred for a further 3 hours at 25° C. and a solution of 0.952 kg of tungsten hexachloride in 2.4 liters of anhydrous methanol is then added over a period of one hour and the mixture is stirred for an additional 3 hours.

The precipitate is filtered off, the methanol is distilled off from the filtrate and the residue is dried under vacuum. A viscous brown product is obtained.

Yield: 88% of theory.
Purity: by nitrogen determination—100%.

EXAMPLE 2

Tungsten hexa(di-2-ethylhexyldithiocarbamate)

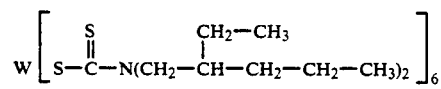

Empirical formula: $C_{102}H_{204}N_6S_{12}W$
Molecular weight: 2083.34

0.72 kg of granulated caustic soda is added to 10 liters of anhydrous methanol and the mixture is stirred until all solid material has dissolved. 4.34 kg of bis-2-ethylhexylamine are added to this solution and 1.1 liters of carbon disulfide are introduced over a period of two hours. The mixture is stirred for a further 3 hours and a solution of 1.19 kg of tungsten hexachloride in 3 liters of anhydrous methanol is then added and the mixture is reacted for 3 hours. The precipitate is filtered off and the solvent is distilled off from the filtrate. The residue, a dark brown pasty product, is dried at 50° C. under vacuum.

Yield: 85% of theory.
Purity: by nitrogen determination—99.6%.

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:
1. A tungsten hexa(dialkyldithiocarbamate) of the formula I

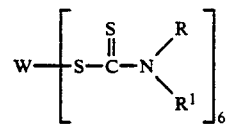

wherein R and $R^1$ may be identical or different and are selected from the group consisting of branched or straight-chain, saturated or unsaturated alkyl radicals having 1-18 carbon atoms.
2. Tungsten hexa(diamyldithiocarbamate).
3. Tungsten hexa(di-2-ethylhexyldithiocarbamate).
4. A process for the preparation of a tungsten hexa(dialkyldithiocarbamate) of formula I in claim 1, comprising reacting in a solvent 1 mol of tungsten hexachloride with 6 mols of an alkali metal dialkyldithiocarbamate of the general formula II

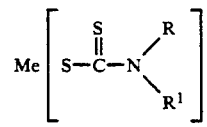

in which R and $R^1$ are as defined in claim 1 and Me represents sodium, potassium or ammonium, separating any sodium chloride, potassium chloride or ammonium chloride formed, and isolating the tungsten hexa(dialkyldithiocarbamate).
5. The process of claim 4, wherein said solvent is an anhydrous solvent.
6. The process of claim 5 wherein said anhydrous solvent is selected from the group consisting of methanol, ethanol, butanol, isopropanol, dioxane, tetrahydrofuran and ethylene glycol monoalkyl ether.
7. The process of claim 4, wherein the reaction is conducted at a temperatures of 10°-90° C.
8. The process of claim 7, wherein the reaction is conducted at a temperatures of 20°-30° C.
9. A composition of matter comprising an oil selected from the group consisting of permanent gear lubricating oils and hydraulic fluids and a tungsten hexa(dialkyldithiocarbamate) of claim 1.
10. The composition of claim 9 wherein said tungsten hexa(dialkyldithiocarbamate) is present in an amount sufficient to prolong the life of said oil.
11. A method of prolonging the life of an oil selected from the group consisting of permanent gear lubricating oils and hydraulic fluids comprising adding to said oil an amount of a tungsten hexa(dialkyldithiocarbamate) of claim 1 sufficient to prolong the life of said oil.
12. A tungsten hexa(dialkyldithiocarbamate) of the formula I

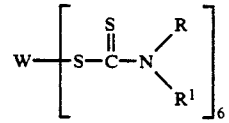

wherein R and $R^1$ may be identical or different and are selected from the group consisting of straight-chain, saturated or unsaturated alkyl radicals having 1-18 carbon atoms.